(12) United States Patent
Murakami et al.

(10) Patent No.: US 8,450,356 B2
(45) Date of Patent: *May 28, 2013

(54) PHARMACEUTICAL COMPOSITION

(75) Inventors: Yasushi Murakami, Yokohama (JP);
Naoko Kobayashi, Yokohama (JP);
Azuma Nishio, Yokohama (JP); Nobuo Kubota, Yokohama (JP)

(73) Assignee: Pola Pharma Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/362,527

(22) Filed: Jan. 31, 2012

(65) Prior Publication Data

US 2012/0129905 A1    May 24, 2012

Related U.S. Application Data

(62) Division of application No. 12/523,067, filed on Jul. 14, 2009.

(30) Foreign Application Priority Data

Jan. 26, 2007   (JP) ................................. 2007-016789

(51) Int. Cl.
*A01N 43/52*  (2006.01)
*A61K 31/415*  (2006.01)
*C07D 233/28*  (2006.01)
*C07D 233/91*  (2006.01)

(52) U.S. Cl.
USPC ..................................... 514/398; 548/327.5

(58) Field of Classification Search
USPC ........................................................ 514/398
See application file for complete search history.

(56) References Cited

U.S. PATENT DOCUMENTS

| | | | |
|---|---|---|---|
| 4,462,992 | A | 7/1984 | Agrawal et al. |
| 4,797,397 | A | 1/1989 | Suto et al. |
| 5,036,060 | A | 7/1991 | Alam et al. |
| 5,270,330 | A | 12/1993 | Suzuki et al. |
| 5,532,380 | A | 7/1996 | Suzuki et al. |
| 5,700,825 | A | 12/1997 | Hofer et al. |
| 5,811,032 | A | 9/1998 | Kawai et al. |
| 5,834,315 | A | 11/1998 | Riesgo et al. |
| 5,961,955 | A | 10/1999 | Shochat et al. |
| 6,165,484 | A | 12/2000 | Raad et al. |
| 7,201,913 | B1 | 4/2007 | Muggetti et al. |
| 2002/0122768 | A1* | 9/2002 | Liu et al. ........................ 424/1.11 |
| 2010/0076042 | A1 | 3/2010 | Murakami et al. |
| 2010/0130576 | A1 | 5/2010 | Murakami et al. |

FOREIGN PATENT DOCUMENTS

| | | |
|---|---|---|
| JP | 3-136306 | 6/1991 |
| JP | 3-223258 | 10/1991 |
| JP | 7-126017 | 5/1995 |
| JP | 9-77667 | 3/1997 |
| JP | 2003-512430 | 4/2003 |
| JP | 2003-321459 | 11/2003 |
| JP | 2005-27515 | 2/2005 |
| JP | 2007-106736 | 4/2007 |
| JP | 2007-191417 | 8/2007 |
| WO | WO 94/14778 | 7/1994 |
| WO | WO 96/17252 | 6/1996 |

OTHER PUBLICATIONS

U.S. Appl. No. 13/362,545, filed Jan. 31, 2012, Murakami, et al.
U.S. Appl. No. 13/365,723, filed Feb. 3, 2012, Murakami, et al.
U.S. Appl. No. 13/365,785, filed Feb. 3, 2012, Murakami, et al.
T. Yahiro, et al., "Effects of Hypoxic Cell Radiosensitizer Doranidazole (PR-350) on the Radioresponse of Murine and Human Tumor Cells in vitro and in vivo", Journal of Radiation Research, vol. 46, No. 3, XP-002584274, Sep. 2005, pp. 363-372.
Natsuo Oya, M.D., et al., "Optical Isomers of a New 2-Nitroimidazole Nucleoside Analog (PR-350 Series): Radiosensitization Efficiency and Toxicity", International Journal of Radiation Oncology Biology Physics, vol. 33, No. 1, XP-002584275, 1995, pp. 119-127.

* cited by examiner

*Primary Examiner* — Shirley V Gembeh
(74) *Attorney, Agent, or Firm* — Oblon, Spivak, McClelland, Maier & Neustadt, L.L.P.

(57) ABSTRACT

To provide a pharmaceutical composition which can enhance the storage stability of 1-(1-hydroxymethyl-2,3-dihydroxypropyloxymethyl)-2-nitroimidazole without impairing the effect of the compound.

The pharmaceutical composition includes 1-(1-hydroxymethyl-2,3-dihydroxypropyloxymethyl)-2-nitroimidazole, which is represented by formula (1):

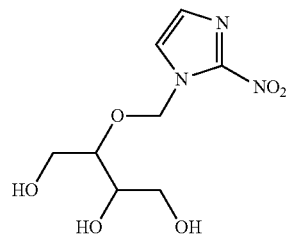

(1)

and a compound having chelating ability.

18 Claims, 6 Drawing Sheets

PHARMACEUTICAL COMPOSITION

CROSS REFERENCE TO RELATED APPLICATION

This application is a divisional of U.S. application Ser. No. 12/523,067, filed Jul. 14, 2009, which is a 371 of PCT/JP08/000040, filed on Jan. 17, 2008, and claims priority to Japanese Patent Application No. 2007-016789, filed on Jan. 26, 2007.

TECHNICAL FIELD

The present invention relates to a pharmaceutical composition and, more particularly, to a pharmaceutical composition for use in cancer radiotherapy.

BACKGROUND ART

In cancer radiotherapy, 2-nitroimidazole derivatives are known to be useful drugs which increase radiation sensitivity of cancer cells with radioresistance in a hypoxic state, and enhance the effect of radiotherapy. Among 2-nitroimidazole derivatives, 1-(1-hydroxymethyl-2,3-dihydroxypropyloxymethyl)-2-nitroimidazole, which is represented by the following formula (1), has particularly high hydrophilicity and virtually no transferability to neurocytes, to thereby serve as a radiation sensitizer having no toxicity to the central nervous system (see, for example Patent Documents 1 to 3). In addition to exhibiting radiation sensitizing effect to hypoxic cells, the compound (1) has hydroxyl-group-removing action in nucleic acid (see, for example, Patent Document 4), apoptosis-signal maintaining action (see, for example, Patent Document 5), etc. Thus, the compound (1) is considered to be a useful drug in cancer therapy.

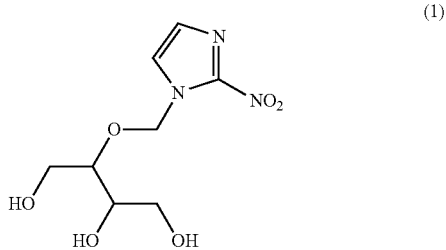 [SMILES: O=[N+]([O-])c1nccn1COC(CO)C(O)CO]

(1)

In general, the action mechanism of a 2-nitroimidazole derivative is thought to include a re-oxidizing step attributed to very strong electron affinity of the 2-position nitro group. However, such an electron affinity of the 2-nitro group also means the instability of the nitro group. Actually, the nitro group is readily decomposed to form nitrogen monoxide or other species. It has also been known that side chain cleavage occurs under acidic conditions, leading to release of 2-nitroimidazole. In other words, stability of 2-nitroimidazole derivatives is thought to be impaired by the 2-position nitro group, which is a target-action-providing group. Therefore, there has been demand for the development of means for enhancing storage stability of 2-nitroimidazole derivatives without impairing the effect thereof.

Meanwhile, several means for stabilizing compounds having a nitro group are known. For example, the means include stabilization by phospholipid (see, for example, Patent Document 6) and stabilization by a buffer such as citric acid-citrate salt or phosphoric acid-phosphate salt (see, for example, Patent Document 7). It has also been known that a chelating agent exhibits a positive effect on stabilization of nitro compounds (see, for example, Patent Document 6). However, there has not been known means for stabilizing the aforementioned 2-nitroimidazole derivatives. Particularly, it has never been known how a chelating agent stabilizes 2-nitroimidazole derivatives.

Patent Document 1: JP-A-1991-223258
Patent Document 2: WO 1994/014778
Patent Document 3: JP-A-2003-321459
Patent Document 4: JP-A-2005-27515
Patent Document 5: JP-A-1997-77667
Patent Document 6: Japanese kohyo Patent Publication No. 2003-512430
Patent Document 7: JP-A-1995-126017

DISCLOSURE OF THE INVENTION

Problems to be Solved by the Invention

The present invention has been accomplished under such circumstances. Thus, an object of the present invention is to provide a pharmaceutical composition which can enhance the storage stability of 1-(1-hydroxymethyl-2,3-dihydroxypropyloxymethyl)-2-nitroimidazole without impairing the effect of the compound.

Means for Solving the Problems

In view of the foregoing, the present inventors have carried out extensive studies, and have found that, through adding a compound having chelating ability to 1-(1-hydroxymethyl-2,3-dihydroxypropyloxymethyl)-2-nitroimidazole, decomposition of the 2-nitro group and release of 2-nitroimidazole can be prevented, while the target effect of 1-(1-hydroxymethyl-2,3-dihydroxypropyloxymethyl)-2-nitroimidazole is maintained. The present invention has been accomplished on the basis of this finding.

Accordingly, the present invention provides a pharmaceutical composition comprising 1-(1-hydroxymethyl-2,3-dihydroxypropyloxymethyl)-2-nitroimidazole, which is represented by formula (1):

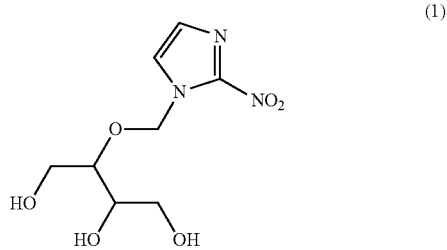 [SMILES: O=[N+]([O-])c1nccn1COC(CO)C(O)CO]

(1)

and a compound having chelating ability.

The present invention also provides use of the composition for producing a radiation sensitizer.

The present invention also provides a cancer radiotherapy, characterized by administering the composition in an effective amount to a subject in need thereof and irradiating the subject.

Effects of the Invention

According to the present invention, the storage stability of 1-(1-hydroxymethyl-2,3-dihydroxypropyloxymethyl)-2-nitroimidazole can be enhanced without impairing the effect thereof; whereby highly effective cancer radiotherapy can be realized.

Figure 1:
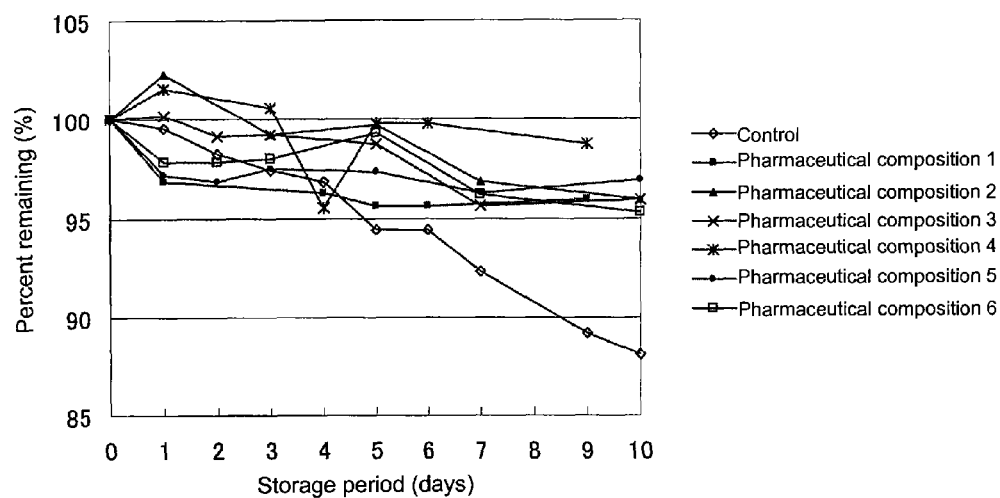
FIG. 1 A graph showing the results of the severe test carried out in Example 1.

BEST MODES FOR CARRYING OUT THE INVENTION 1-(1-Hydroxymethyl-2,3-dihydroxypropyloxymethyl)-2-nitroimidazole (compound (1)) employed in the present invention includes four stereoisomers: RS form, SR form, RR form, and SS form. In the present invention, each of the optically active substances or a mixture thereof such as a racemic mixture of species of the optically active substances may be used. From the viewpoint of efficacy, particularly preferred is a racemic mixture of an isomer having a stereo-structure represented by formula (2) (SR form) and an isomer having a stereo-structure represented by formula (3) (RS form).

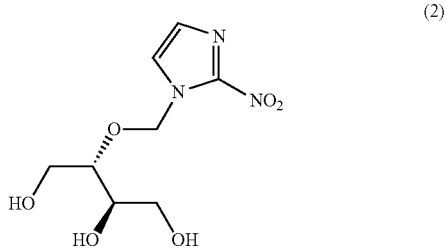

(2)

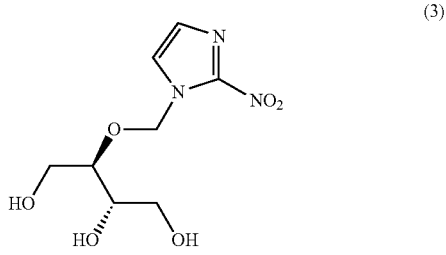

(3)

In clinical tests, compound (1) is required to be stored at 5° C. before tests in order to ensure stability of the compound. Thus, considerable difficulty is encountered in handling compound (1), which must be stored under the above conditions. Compound (1) may be produced through a method disclosed in Patent Document 1 or 2. In one specific production procedure, 2-nitro-1-trimethylsilylimidazole is condensed with 2-acetoxymethoxy-1,3,4-triacetoxybutane in the presence of a Lewis acid, followed by deacetylation through reaction with sodium methoxide or a similar substance. In this case, stereo-characteristics of 2-acetoxymethoxy-1,3,4-triacetoxybutane are maintained in the final product, 1-(1-hydroxymethyl-2,3-dihydroxypropyloxymethyl)-2-nitroimidazole.

The content of compound (1) in the pharmaceutical composition of the present invention is preferably 1 to 10 mass %, more preferably 2 to 8 mass %. When the compound (1) content is excessively small, the amount of 1-(1-hydroxymethyl-2,3-dihydroxypropyloxymethyl)-2-nitroimidazole in the produced pharmaceutical formulation is insufficient, impeding the effect of compound (1), whereas when the amount is excessively large, in some cases a portion of the compound cannot be dissolved in a vehicle, impairing the stability of the formulation.

No particular limitation is imposed on the compound having chelating ability employed in the present invention, so long as the compound can be employed as an additive for pharmaceutical products. Examples of such compounds include aldonic acids such as gluconic acid and gluceptic acid; aldaric acids such as tartaric acid and glucaric acid; uronic acids such as glucuronic acid; saccharic acids or a salt thereof such as ascorbic acid; aminopolycarboxylic acids or a salt thereof such as edetic acid and pentetic acid; oxycarboxylic acids or a salt thereof such as citric acid; amine compounds such as diethylamine; and polyoxyethylene castor oils such as polyoxyl 35 castor oil. Of these, saccharic acids or a salt thereof, aminopolycarboxylic acids or a salt thereof, and amine compounds are preferred, with tartaric acid or a salt thereof, ascorbic acid or a salt thereof, pentetic acid or a salt thereof, and diethylamine being particularly preferred.

Examples of preferred salts include alkali metal salts such as sodium salts and potassium salts; alkaline earth metal salts such as calcium salts and magnesium salts; organic amine salts such as ammonium salts, triethylamine salts, triethanolamine salts, and monoethanolamine salts; and basic amino acid salts such as lysine salts and alginic acid salts. These compounds having chelating ability may be employed in the composition singly or in combination of two or more species.

The amount of compound having chelating ability contained in the pharmaceutical composition of the invention is preferably 0.005 to 5 mass %, more preferably 0.01 to 2 mass %. When the amount of compound having chelating ability is excessively small, stability-enhancing effect may fail to be attained, whereas when the amount is excessively large, the stabilization effect attributed to addition reach a plateau, and formulation of interest may fail to be prepared.

Specifically, when a saccharic acid or a salt thereof is employed, the amount is preferably 0.01 to 2 mass %, more preferably 0.025 to 1.1 mass %. When an aminopolycarboxylic acid or a salt thereof such as edetic acid or a salt thereof, pentetic acid, or calcium trisodium pentetate is employed, the amount is preferably 0.01 to 2 mass %, more preferably 0.01 to 1.0 mass %. Particularly when pentasodium pentetate is employed, the amount is preferably 0.01 to 0.8 mass %, more preferably 0.01 to 0.5 mass %. When an oxycarboxylic acid or a salt thereof is employed, the amount is preferably 0.01 to 2 mass %, more preferably 0.02 to 1 mass %. When an amine compound is employed, the amount is preferably 0.01 to 0.1 mass %, more preferably 0.01 to 0.08 mass %. When a polyoxyethylene castor oil is employed, the amount is preferably 0.01 to 0.8 mass %, more preferably 0.01 to 0.5 mass %.

The pharmaceutical composition of the present invention is preferably employed as a drug, particularly for the purpose of cancer therapy, inter alia, enhancing radiation sensitivity of hypoxic cancer cells in cancer radiotherapy. Examples of the cancer to be preferably treated by the pharmaceutical composition include lung cancer and pancreatic cancer. In a specific procedure of cancer radiotherapy, the composition of the present invention is administered to a patient, and the patient is irradiated.

No particular limitation is imposed on the dosage form of the pharmaceutical composition, and the form may be appropriately selected in accordance with the therapeutic purpose. Examples of the dosage form include oral forms such as tablets, capsules, granules, film-coated drugs, powder, and syrup; and parenteral forms such as injection formulation, suppositories, inhalation, percutaneously absorbable agents, eye drops, and nasal drops. Among them, injection formulation is preferred from the viewpoint of rapid metabolism. The type of injection formulation includes formulations for dripping. A dripping formulation is preferred for the following reason. The dose of a formulation containing 1-(1-hydroxymethyl-2,3-dihydroxypropyloxymethyl)-2-nitroimidazole, an effective ingredient, is increased, since a large amount of the effective ingredient must be administered. In this case, a single dose administration may cause a risky state of the relevant patient. No particular limitation is imposed on the form of such an injection solution, and it may be a solution or a freeze-dry formulation. However, a solution is preferred, since a satisfactory solubility can be attained. Example of preferred vehicles for the solution include pure water, physiological saline, and glucose solution which may be isotonified.

The pharmaceutical composition of the present invention may further contain any of the formulation ingredients generally employed in preparation of drugs, so long as the effect of the present invention is not impaired. Examples of such optional ingredients include polyhydric alcohols such as Macrogol; tonicity agents such as sodium chloride; buffer salts such as phosphate salt; excipients such as crystalline cellulose and starch; nonionic surfactants such as polyoxyethylene-hardened castor oil; anionic surfactants such as sodium lauryl sulfate; viscosity-increasing polysaccharides such as gum arabic; lubricants such as magnesium stearate; colorants; flavoring agents/deodorants; binders such as hydroxypropyl cellulose; and coating agents such as "Eudragit" (registered trademark). In the case of an injection liquid, a particularly preferred formulation contains only compound (1), a compound having chelating ability, and a vehicle, and does not contain other ingredients.

The pharmaceutical composition of the present invention may be produced through processing the aforementioned essential ingredients and optional ingredients in a routine manner.

The dose of the pharmaceutical composition of the present invention may be appropriately selected in consideration of the body weight, age, sex, symptom, etc. of a patient. Generally, the daily dose for an adult is preferably 1 to 10 g as 1-(1-hydroxymethyl-2,3-dihydroxypropyloxymethyl)-2-nitroimidazole.

EXAMPLES

The present invention will next be described in more detail by way of examples, which should not be construed as limiting the invention thereto.

Example 1

Solutions for drip infusion (i.e., pharmaceutical compositions 1 to 6), which are pharmaceutical compositions of the present invention, were prepared according to the below-described formulations. Specifically, the formulated ingredients were weighed and placed in a container, and the mixture was stirred for dissolution. Each of the formulated products was stored for 9 or 10 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 1 shows the results.

As is clear from FIG. 1, 1-(1-hydroxymethyl-2,3-dihydroxypropyloxymethyl)-2-nitroimidazole has been found to be stable in the pharmaceutical compositions of the present invention, even under severe conditions.

TABLE 1

| Ingredients | (mass %) |
| --- | --- |
| Compound (1) (racemic) | 5 |
| Chelating compound | amount in Table 2 |
| Water | balance |
| Total | 100 |

TABLE 2

| Samples | Chelating compound | (mass %) |
| --- | --- | --- |
| Pharmaceutical compn. 1 | Calcium saccharate*[1] | 0.3 |
| Pharmaceutical compn. 2 | Calcium disodium edetate | 0.04 |
| Pharmaceutical compn. 3 | Calcium gluconate | 0.025 |
| Pharmaceutical compn. 4 | Magnesium gluconate | 1.1 |
| Pharmaceutical compn. 5 | Trisodium citrate | 0.9 |
| Pharmaceutical compn. 6 | Disodium hydrogencitrate | 0.02 |
| Control |  | 0.0 |

*[1]Calcium saccharate: defined in Japanese Pharmaceutical Excipients

Example 2

Figure 2:
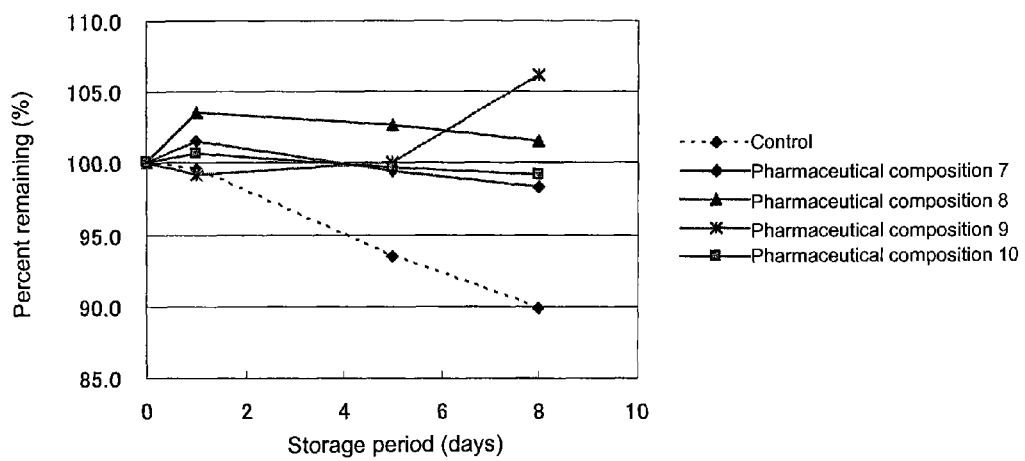
FIG. 2 A graph showing the results of the severe test carried out in Example 2.

In a manner similar to that of Example 1, solutions for drip infusion (i.e., pharmaceutical compositions 7 to 10), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 2 shows the results.

As is clear from FIG. 2, 1-(1-hydroxymethyl-2,3-dihydroxypropyloxymethyl)-2-nitroimidazole has been found to be stable in the pharmaceutical compositions of the present invention, even under severe conditions.

TABLE 3

| Ingredients | (mass %) |
| --- | --- |
| Compound (1) (racemic) | 5 |
| Calcium trisodium pentetate | amount in Table 4 |
| Water | balance |
| Total | 100 |

TABLE 4

| Samples | Calcium trisodium pentetate (mass %) |
| --- | --- |
| Pharmaceutical compn. 7 | 0.01 |
| Pharmaceutical compn. 8 | 0.05 |
| Pharmaceutical compn. 9 | 0.1 |
| Pharmaceutical compn. 10 | 1.0 |
| Control | 0.0 |

Example 3

Figure 3:
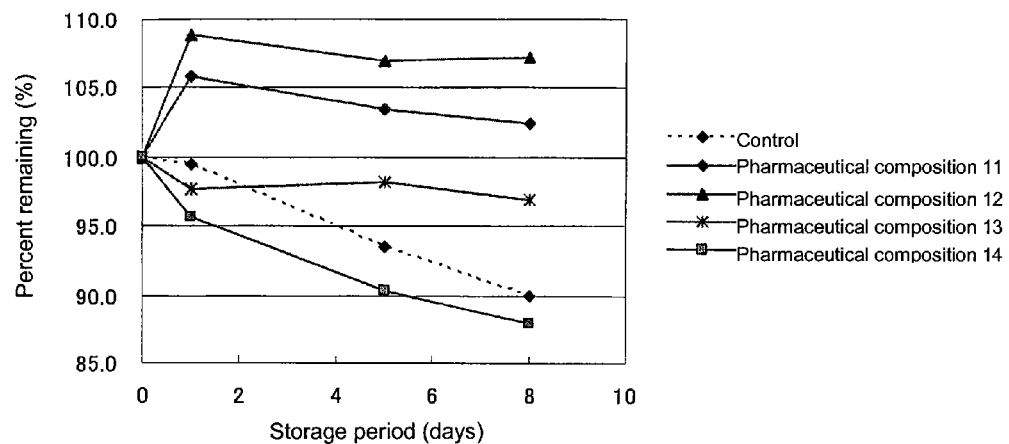
FIG. 3 A graph showing the results of the severe test carried out in Example 3.

In a manner similar to that of Example 1, solutions for drip infusion (i.e., pharmaceutical compositions 11 to 14), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 3 shows the results.

As is clear from FIG. 3, 1-(1-hydroxymethyl-2,3-dihydroxypropyloxymethyl)-2-nitroimidazole has been found to be stable in the pharmaceutical compositions of the present invention, even under severe conditions.

TABLE 5

| Ingredients | (mass %) |
| --- | --- |
| Compound (1) (racemic) | 5 |
| Pentasodium pentetate | amount in Table 6 |
| Water | balance |
| Total | 100 |

TABLE 6

| Samples | Pentasodium pentetate (mass %) |
| --- | --- |
| Pharmaceutical compn. 11 | 0.01 |
| Pharmaceutical compn. 12 | 0.05 |
| Pharmaceutical compn. 13 | 0.1 |
| Pharmaceutical compn. 14 | 1.0 |
| Control | 0.0 |

Example 4

Figure 4:
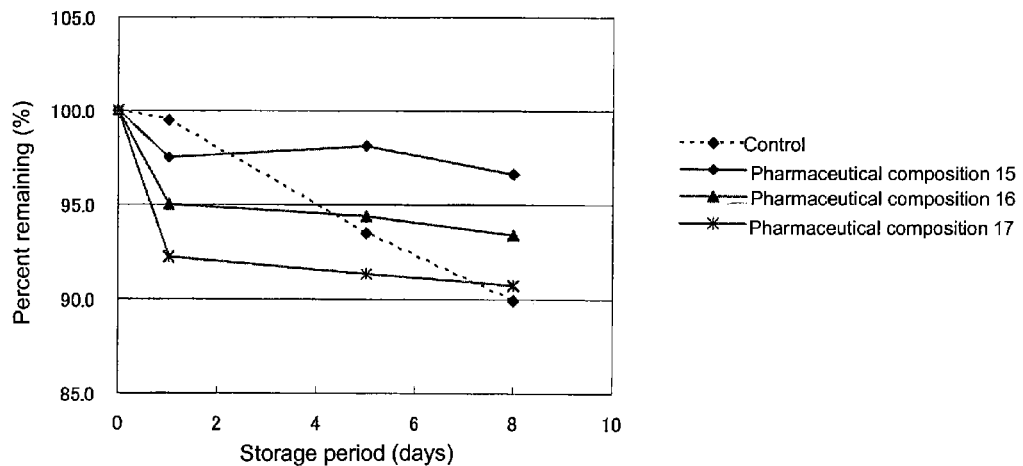
FIG. 4 A graph showing the results of the severe test carried out in Example 4.

In a manner similar to that of Example 1, solutions for drip infusion (i.e., pharmaceutical compositions 15 to 17), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 4 shows the results.

As is clear from FIG. 4, 1-(1-hydroxymethyl-2,3-dihydroxypropyloxymethyl)-2-nitroimidazole has been found to be stable in the pharmaceutical compositions of the present invention, even under severe conditions.

TABLE 7

| Ingredients | (mass %) |
| --- | --- |
| Compound (1) (racemic) | 5 |
| Diethylamine | amount in Table 8 |
| Water | balance |
| Total | 100 |

TABLE 8

| Samples | Diethylamine (mass %) |
| --- | --- |
| Pharmaceutical compn. 15 | 0.01 |
| Pharmaceutical compn. 16 | 0.05 |
| Pharmaceutical compn. 17 | 0.1 |
| Control | 0.0 |

Example 5

Figure 5:
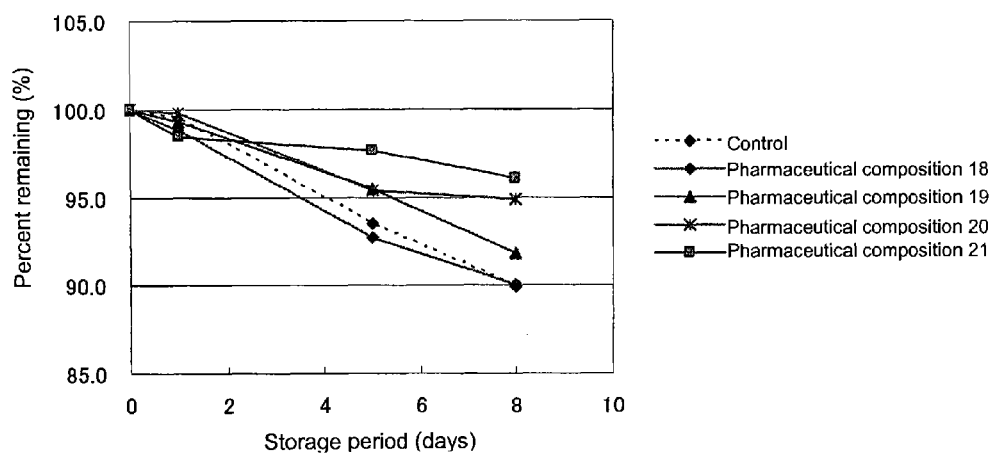
FIG. 5 A graph showing the results of the severe test carried out in Example 5.

In a manner similar to that of Example 1, solutions for drip infusion (i.e., pharmaceutical compositions 18 to 21), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 5 shows the results.

As is clear from FIG. 5, 1-(1-hydroxymethyl-2,3-dihydroxypropyloxymethyl)-2-nitroimidazole has been found to be stable in the pharmaceutical compositions of the present invention, even under severe conditions.

TABLE 9

| Ingredients | (mass %) |
| --- | --- |
| Compound (1) (racemic) | 5 |
| Polyoxyl 35 castor oil | amount in Table 10 |
| Water | balance |
| Total | 100 |

TABLE 10

| Samples | Polyoxyl 35 castor oil (mass %) |
| --- | --- |
| Pharmaceutical compn. 18 | 0.01 |
| Pharmaceutical compn. 19 | 0.05 |
| Pharmaceutical compn. 20 | 0.1 |
| Pharmaceutical compn. 21 | 1.0 |
| Control | 0.0 |

Example 6

Figure 6:
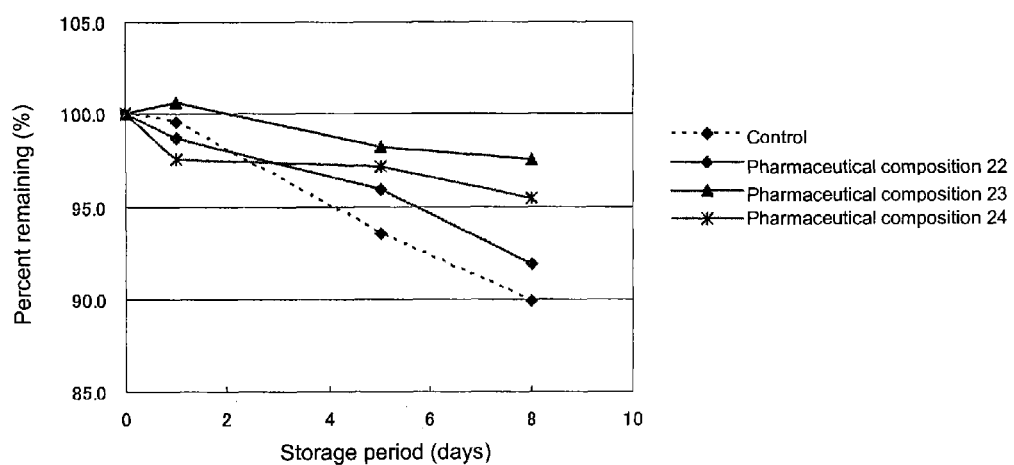
FIG. 6 A graph showing the results of the severe test carried out in Example 6.

In a manner similar to that of Example 1, solutions for drip infusion (i.e., pharmaceutical compositions 22 to 24), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 6 shows the results.

As is clear from FIG. 6, 1-(1-hydroxymethyl-2,3-dihydroxypropyloxymethyl)-2-nitroimidazole has been found to be stable in the pharmaceutical compositions of the present invention, even under severe conditions.

TABLE 11

| Ingredients | (mass %) |
|---|---|
| Compound (1) (racemic) | 5 |
| Sodium ascorbate | amount in Table 12 |
| Water | balance |
| Total | 100 |

TABLE 12

| Samples | Sodium ascorbate (mass %) |
|---|---|
| Pharmaceutical compn. 22 | 0.01 |
| Pharmaceutical compn. 23 | 0.05 |
| Pharmaceutical compn. 24 | 0.1 |
| Control | 0.0 |

Example 7

Figure 7:
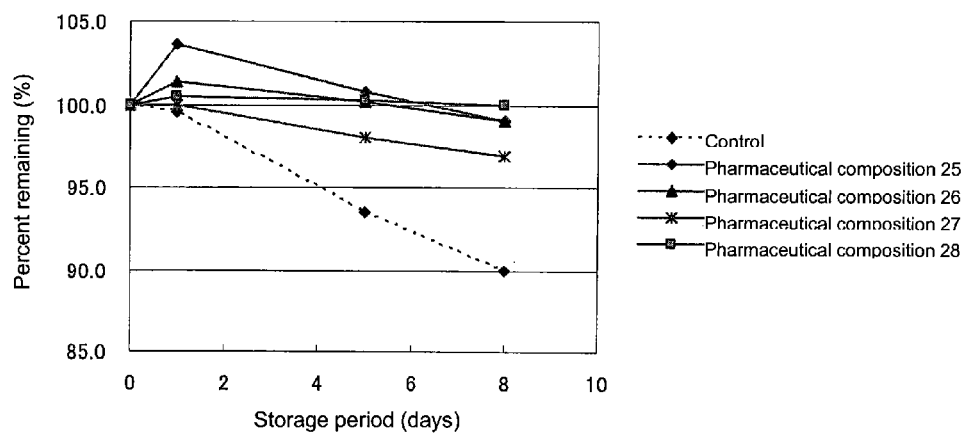
FIG. 7 A graph showing the results of the severe test carried out in Example 7.

In a manner similar to that of Example 1, solutions for drip infusion (i.e., pharmaceutical compositions 25 to 28), which are pharmaceutical compositions of the present invention, were prepared according to the below-described formulations. Each of the formulated products was stored for 8 days under severe conditions (55° C.), and the 1-(1-hydroxymethyl-2,3-dihydroxypropyloxymethyl)-2-nitroimidazole content of the product was periodically quantitated. As a control, a 5 mass % aqueous solution of compound (1) was employed. FIG. 7 shows the results.

As is clear from FIG. 7, 1-(1-hydroxymethyl-2,3-dihydroxypropyloxymethyl)-2-nitroimidazole has been found to be stable in the pharmaceutical compositions of the present invention, even under severe conditions.

TABLE 13

| Ingredients | (mass %) |
|---|---|
| Compound (1) (racemic) | 5 |
| Sodium tartrate dihydrate | amount in Table 14 |
| Water | balance |
| Total | 100 |

TABLE 14

| Samples | Sodium tartrate dihydrate (mass %) |
|---|---|
| Pharmaceutical compn. 25 | 0.01 |
| Pharmaceutical compn. 26 | 0.05 |
| Pharmaceutical compn. 27 | 0.1 |
| Pharmaceutical compn. 28 | 1.0 |
| Control | 0.0 |

Example 8

Figure 8:
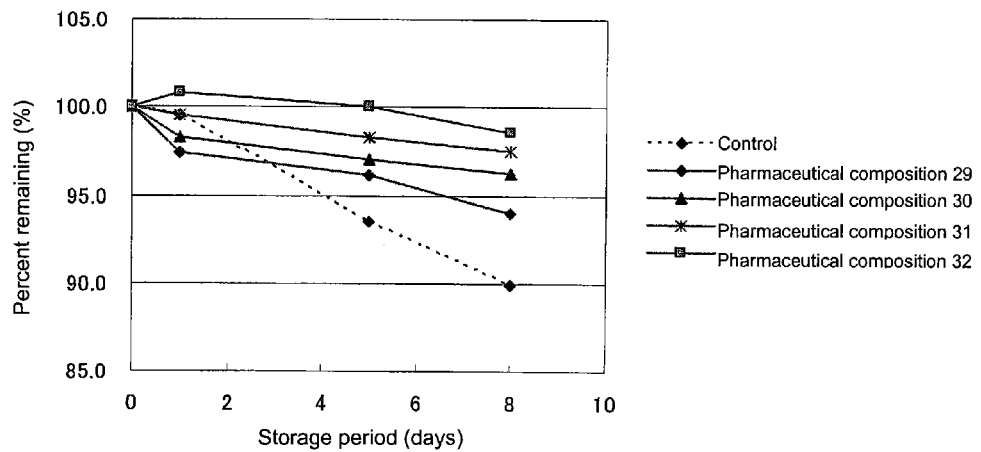
FIG. 8 A graph showing the results of the severe test carried out in Example 8.

In a manner similar to that of Example 1, solutions for drip infusion (i.e., pharmaceutical compositions 29 to 32), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 8 shows the results.

As is clear from FIG. 8, 1-(1-hydroxymethyl-2,3-dihydroxypropyloxymethyl)-2-nitroimidazole has been found to be stable in the pharmaceutical compositions of the present invention, even under severe conditions.

TABLE 15

| Ingredients | (mass %) |
|---|---|
| Compound (1) (racemic) | 5 |
| Calcium gluceptate | amount in Table 16 |
| Water | balance |
| Total | 100 |

TABLE 16

| Samples | Calcium gluceptate (mass %) |
|---|---|
| Pharmaceutical compn. 29 | 0.01 |
| Pharmaceutical compn. 30 | 0.05 |
| Pharmaceutical compn. 31 | 0.1 |
| Pharmaceutical compn. 32 | 1.0 |
| Control | 0.0 |

Example 9

Figure 9:
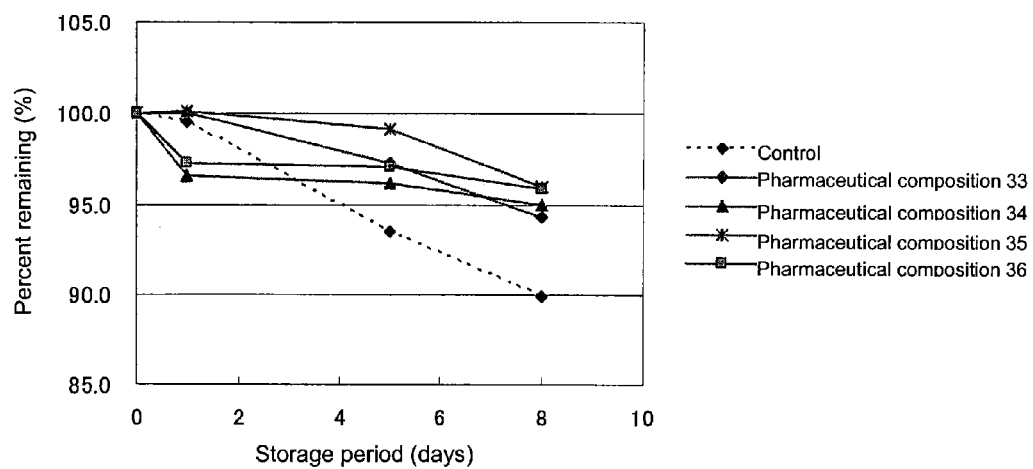
FIG. 9 A graph showing the results of the severe test carried out in Example 9.

In a manner similar to that of Example 1, solutions for drip infusion (i.e., pharmaceutical compositions 33 to 36), which are pharmaceutical compositions of the present invention, were prepared according to the below-described formulations. Each of the formulated products was stored for 8 days under severe conditions (55° C.), and the content of 1-(1-hydroxymethyl-2,3-dihydroxypropyloxymethyl)-2-nitroimidazole in the product was periodically quantitated. As a control, a 5 mass % aqueous solution of compound (1) was employed. FIG. 9 shows the results.

As is clear from FIG. 9, 1-(1-hydroxymethyl-2,3-dihydroxypropyloxymethyl)-2-nitroimidazole has been found to be stable in the pharmaceutical compositions of the present invention, even under severe conditions.

TABLE 17

| Ingredients | (mass %) |
|---|---|
| Compound (1) (racemic) | 5 |
| Sodium gluceptate | amount in Table 18 |
| Water | balance |
| Total | 100 |

TABLE 18

| Samples | Sodium gluceptate (mass %) |
| --- | --- |
| Pharmaceutical compn. 33 | 0.01 |
| Pharmaceutical compn. 34 | 0.05 |
| Pharmaceutical compn. 35 | 0.1 |
| Pharmaceutical compn. 36 | 1.0 |
| Control | 0.0 |

Comparative Example 1

The procedure of Example 1 was repeated, except that a phosphate salt having only a buffer action was used instead of a compound having chelating ability, to thereby prepare solutions for drip infusion according to the below-described formulations. As a control, a 5 mass % aqueous solution of compound (1) was employed. The pharmaceutical formulations were subjected to a storage test under sever conditions (55° C.) for 10 days. The results are shown in FIG. 10.

Figure 10:
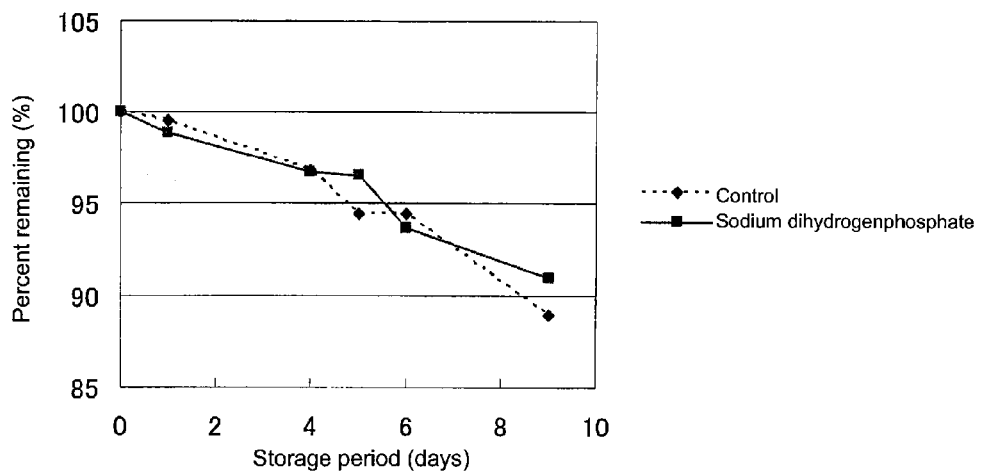
FIG. 10 A graph showing the results of the severe test carried out in Comparative Example 1.

As is clear from FIG. 10, the composition containing a phosphate salt exhibited a compound (1) content of less than 95 mass % on day 9, indicating the effect of a compound having chelating ability. Therefore, the effect of the pharmaceutical composition of the present invention was found to be attained not by a buffer action of the salt but by a chelating action.

TABLE 19

| Ingredients | (mass %) |
| --- | --- |
| Compound (1) (racemic) | 5 |
| Sodium dihydrogenphosphate*[1] | 0.25 |
| Water | balance |
| Total | 100 |

*[1]dihydrate

Test Example 1

The radiation sensitization effect of the present invention was investigated through the micronucleus method by use of mouse squamous cell carcinoma cells (SCCVII).

Figure 11:
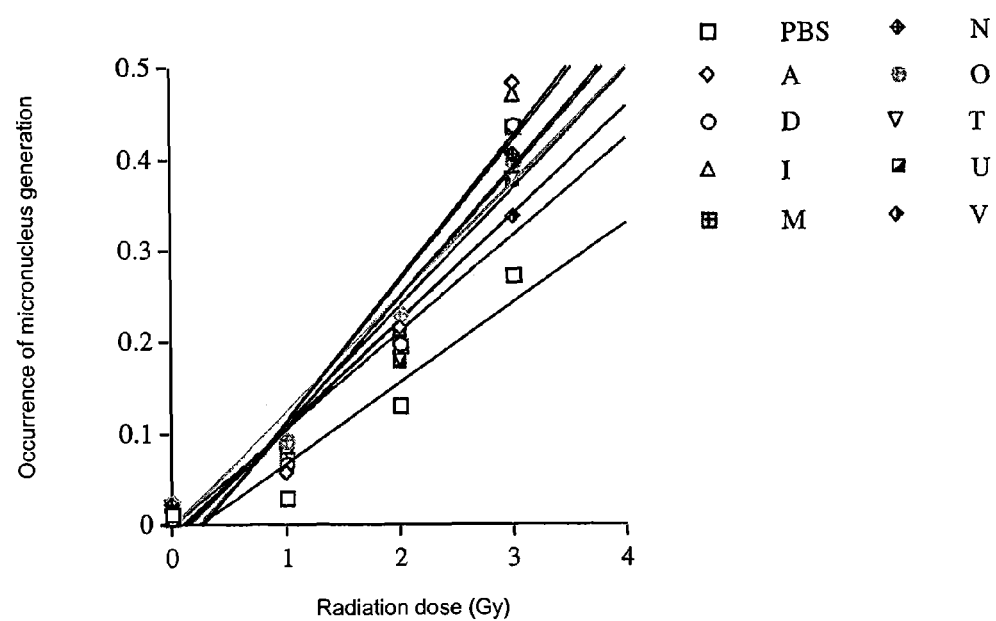
FIG. 11 A graph showing the radiation sensitization effects of the tested pharmaceutical compositions.

Specifically, a gas (95% $N_2$+5% $CO_2$) was caused to pass through mouse squamous cell carcinoma cells (SCCVII) for 20 minutes, to thereby render the cells in a hypoxic state. Subsequently, in the presence of PBS and a test pharmaceutical formulation, the cells were irradiated with X-rays (0, 1, 2, or 3 Gy). The following tested pharmaceutical formulations were employed: pharmaceutical composition 10 (Example 2), pharmaceutical composition 12 (Example 3), pharmaceutical composition 15 (Example 4), pharmaceutical composition 21 (Example 5), pharmaceutical composition 23 (Example 6), pharmaceutical composition 28 (Example 7), pharmaceutical composition 32 (Example 8), and pharmaceutical composition 36 (Example 9). A 5 mass % aqueous solution of compound (1) (racemic) was employed as a control. After irradiation, the cells were washed and cultured for about 24 hours in the presence of cytochalasin B, to thereby generate binucleate cells. The thus-treated cells were fixed and fluoro-stained, and the number of binucleate cells and that of micronuclei were counted, whereby occurrence of micronucleus generation was determined. FIG. 11 shows the results.

In FIG. 11, "A" denotes control, "D" denotes pharmaceutical composition 15, "I" denotes pharmaceutical composition 23, "M" denotes pharmaceutical composition 28, "N" denotes pharmaceutical composition 12, "O" denotes pharmaceutical composition 10, "T" denotes pharmaceutical composition 21, "U" denotes pharmaceutical composition 32, and "V" denotes pharmaceutical composition 36. In non-irradiated groups, occurrence of micronucleus generation was not changed by PBS or any of the tested formulations. No direct effect of the formulations on the cells was observed. In other words, direct toxicity to the cells by the additives was not observed. In contrast, in irradiated groups, all tested formulations exhibited radiation sensitization effect in a hypoxic state. In particular, pharmaceutical compositions 10, 12, 15, 23, and 28 did not vary the sensitization effect, as compared with a control containing no compound having chelating ability.

The invention claimed is:
1. A method of producing a radiation sensitizer composition having enhanced storage stability consisting essentially of a radiation sensitizer compound and a compound having chelating ability, wherein the method comprises:
combining a 1-(1-hydroxymethyl-2,3-dihydroxypropyloxymethyl)-2-nitroimidazole radiation sensitizer compound represented by formula (1):

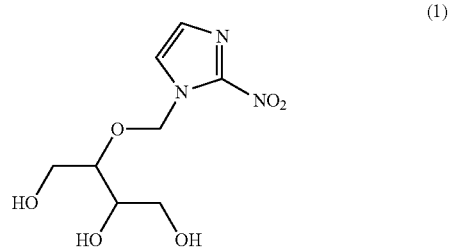 [SMILES: O=[N+]([O-])c1nccn1COC(CO)C(O)CO]

and a compound having chelating ability selected from the group consisting of a saccharic acid, a salt of a saccharic acid, an aminopolycarboxylic acid, a salt of an aminopolycarboxylic acid, an oxycarboxylic acid, a salt of an oxycarboxylic acid, an amine compound, a polyoxyethylene castor oil, and mixtures thereof.
2. The method of claim 1, wherein the compound having chelating ability is an alkaline earth metal salt of gluconic acid, gluceptic acid, tartaric acid, glucuronic acid, glucaric acid, or ascorbic acid.
3. The method of claim 1, wherein the compound represented by formula (1) is an RS•SR racemic mixture of an isomer having a stereo-structure represented by formula (2):

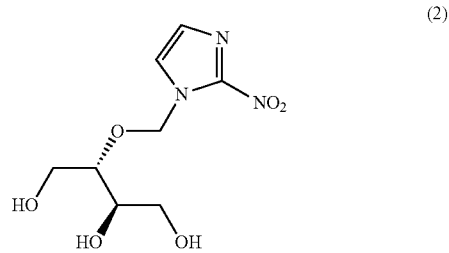 [SMILES: O=[N+]([O-])c1nccn1CO[C@@H](CO)[C@H](O)CO]

and an isomer having a stereo-structure represented by formula (3):

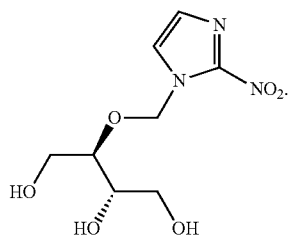

(3)

4. The method of claim 1, wherein the radiation sensitizer composition is an injection composition.

5. The method of claim 1, wherein the radiation sensitizer composition contains the compound represented by formula (1) in an amount of 1 to 10 mass %.

6. The method of producing a radiation sensitizer composition of claim 1, wherein the compound represented by formula (1) in present in an amount of 2 to 8 mass %.

7. The method of producing a radiation sensitizer composition of claim 1, wherein the compound having chelating ability comprises diethylamine.

8. The method of producing a radiation sensitizer composition of claim 1, wherein the compound having chelating ability is a saccharic acid or a salt of a saccharic acid in an amount of 0.025 to 1.1 mass %; an aminopolycarboxylic acid or a salt of an aminopolycarboxylic acid in an amount of 0.01 to 1.0 mass %; an oxycarboxylic acid or a salt of an oxycarboxylic acid in an amount of 0.02 to 1 mass %; an amine compound in an amount of 0.01 to 0.1 mass %; or a polyoxyethylene caster oil in an amount of 0.01 to 0.8 mass %.

9. The method of producing a radiation sensitizer composition of claim 1, wherein the compound having chelating ability is present an amount of 0.01 to 2 mass %.

10. The method of producing a radiation sensitizer composition of claim 1, wherein the compound having chelating ability is a saccharic acid or a salt of a saccharic acid in an amount of 0.025 to 1.1 mass %.

11. The method of producing a radiation sensitizer composition of claim 1, wherein the compound having chelating ability is an aminopolycarboxylic acid or a salt of an aminopolycarboxylic acid in an amount of 0.01 to 1.0 mass %.

12. The method of producing a radiation sensitizer composition of claim 1, wherein the compound having chelating ability is an oxycarboxylic acid or a salt of an oxycarboxylic acid in an amount of 0.02 to 1 mass %.

13. The method of producing a radiation sensitizer composition of claim 1, wherein the compound having chelating ability is an amine compound in an amount of 0.01 to 0.1 mass %.

14. The method of producing a radiation sensitizer composition of claim 1, wherein the compound having chelating ability is a polyoxyethylene caster oil in an amount of 0.01 to 0.8 mass %.

15. The method of producing a radiation sensitizer composition of claim 1, wherein the compound having chelating ability is edetic acid, a salt of edetic acid, pentetic acid, or a salt of pentetic acid.

16. The method of producing a radiation sensitizer composition of claim 1, wherein the compound having chelating ability is calcium trisodium pentetate or pentasodium pentetate.

17. The method of producing a radiation sensitizer composition of claim 1, wherein the compound represented by formula (1) is at least one member selected from the group consisting of the RS form, SR form, RR form, and SS form of the compound represented by formula (1).

18. The method of producing a radiation sensitizer composition of claim 17, wherein the compound represented by formula (1) is an optically active stereoisomer selected from the group consisting of the RS form, SR form, RR form, and SS form of the compound represented by formula (1).

* * * * *